(12) United States Patent
Mount

(10) Patent No.: US 11,759,542 B2
(45) Date of Patent: Sep. 19, 2023

(54) SYSTEM FOR REDUCING AIRBORNE CONTAMINANTS

(71) Applicant: Randy A. Mount, Dayton, OH (US)

(72) Inventor: Randy A. Mount, Dayton, OH (US)

( * ) Notice: Subject to any disclaimer, the term of this patent is extended or adjusted under 35 U.S.C. 154(b) by 0 days.

(21) Appl. No.: 17/412,513

(22) Filed: Aug. 26, 2021

(65) Prior Publication Data

US 2022/0062490 A1 Mar. 3, 2022

Related U.S. Application Data

(60) Provisional application No. 63/070,339, filed on Aug. 26, 2020.

(51) Int. Cl.
*A61L 9/20* (2006.01)

(52) U.S. Cl.
CPC ........... *A61L 9/205* (2013.01); *A61L 2209/15* (2013.01)

(58) Field of Classification Search
CPC ... A61L 9/205; A61L 9/20; A61L 9/18; A61L 9/16; A61L 9/02; A61L 9/04; A61L 9/015; A61L 2209/14; A61L 2209/15; A61L 2209/131; A61L 2209/12; A61L 9/22; B03C 3/60; B03C 3/08; B03C 3/016; B01D 53/885; B01D 2259/804; B01D 2255/802; B01D 53/8668; B01D 2255/2065; B01D 2255/20707; B01D 2255/209; B01D 2255/2094; B01D 2255/9202; B01D 2257/708; B01D 2257/91; B01D 2258/06; B01D 2259/4508

See application file for complete search history.

(56) References Cited

U.S. PATENT DOCUMENTS 6,090,346 A * 7/2000 Rose .......................... A61L 2/02 422/128

FOREIGN PATENT DOCUMENTS

| JP | 2001104458 A | * | 4/2001 | | |
|---|---|---|---|---|---|
| JP | 2002-361095 | * | 12/2002 | | |
| KR | 20130024642 A | * | 3/2013 | | |
| WO | WO-03045534 A1 | * | 6/2003 | ............. | A61L 9/015 |
| WO | WO-2019147058 A1 | * | 8/2019 | ............. | A61L 9/205 |

OTHER PUBLICATIONS

Machine translation of JP2002-361095 (Year: 2002).*

* cited by examiner

*Primary Examiner* — Xiuyu Tai
(74) *Attorney, Agent, or Firm* — Thomas E. Lees, LLC

(57) ABSTRACT

A photocatalytic system for reducing airborne contaminants using an ultraviolet (UV) emitter and photocatalytic cells, the system comprises four (4) photocatalytic cells that, in combination, substantially form an enclosure for the UV emitter. Each photocatalytic cell is positioned at an angle with reference to its adjacent photocatalytic cell.

8 Claims, 2 Drawing Sheets

SYSTEM FOR REDUCING AIRBORNE CONTAMINANTS

CROSS REFERENCE TO RELATED APPLICATIONS

This application claims the benefit of U.S. provisional patent application Ser. No. 63/070,339, filed Aug. 26, 2020, having the title "System for Reducing Airborne Contaminants," which is incorporated herein by reference in its entirety.

FIELD OF THE DISCLOSURE

The present disclosure relates generally to reducing airborne contaminants and, more particularly, to reducing airborne contaminants using ultraviolet (UV) energy.

DESCRIPTION OF RELATED ART

Ultraviolet (UV) light is a form of electromagnetic radiation with wavelength shorter than that of visible light, but with a wavelength longer than X-rays. UV light is known to interact with organic molecules. More particularly, deoxyribonucleic acid (DNA), ribonucleic acid (RNA), and proteins can absorb deep UV light, e.g., in the range of 200 nanometers (nm) to 300 nm, which can lead to rupture of a cell, disruption of DNA replication, and other molecular damage. As such, UV light is sometimes used to disinfect surfaces that might contain bacteria, mold, virus, etc.

SUMMARY

The present disclosure is directed to photocatalytic systems for reducing airborne contaminants using an ultraviolet (UV) emitter and photocatalytic cells.

In some embodiments, a photocatalytic system is disclosed for reducing airborne contaminants using an ultraviolet (UV) emitter and photocatalytic cells. The system comprises four (4) photocatalytic cells that, in combination, substantially form an enclosure for the UV emitter. Each photocatalytic cell is positioned at an angle with reference to its adjacent photocatalytic cell.

Other systems, devices, methods, features, and advantages will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION OF THE EMBODIMENTS

In the presence of ultraviolet (UV) energy, photocatalytic cells produce cluster ions or ionized clouds that reduce airborne contaminants, such as bacteria, mold, or virus. As air passes through the photocatalytic cells, UV energy that strikes the photocatalytic cells results in a catalytic reaction that produces ionized molecules within the airflow. The ionized molecules neutralize some or all of the contaminants that are present in the air.

The effectiveness of photocatalytic systems depends on the concentration of ionized molecules. The concentration of ionized molecules is, in turn, dependent on both: (a) the amount of photocatalytic material on the photocatalytic cells (e.g., titanium dioxide coated on honeycomb structured cells); and, also (b) how much UV strikes the photocatalytic material. In other words, merely having more photocatalytic material (e.g., titanium dioxide) is insufficient if the photocatalytic material is not exposed to the UV energy.

To mitigate losses in efficiency systems are disclosed, which provide for greater UV exposure to photocatalytic materials in a fluid flow path. Specifically, some embodiments include four (4) photocatalytic cells that, in combination, substantially form porous walls of an enclosure for a UV emitter. Each photocatalytic cell is positioned at an angle with reference to its adjacent photocatalytic cell in such a way that two (2) of the photocatalytic cells are located in the fluid flow path before the UV emitter, while two (2) remaining photocatalytic cells are located in the fluid flow path after the UV emitter.

Figure 1:
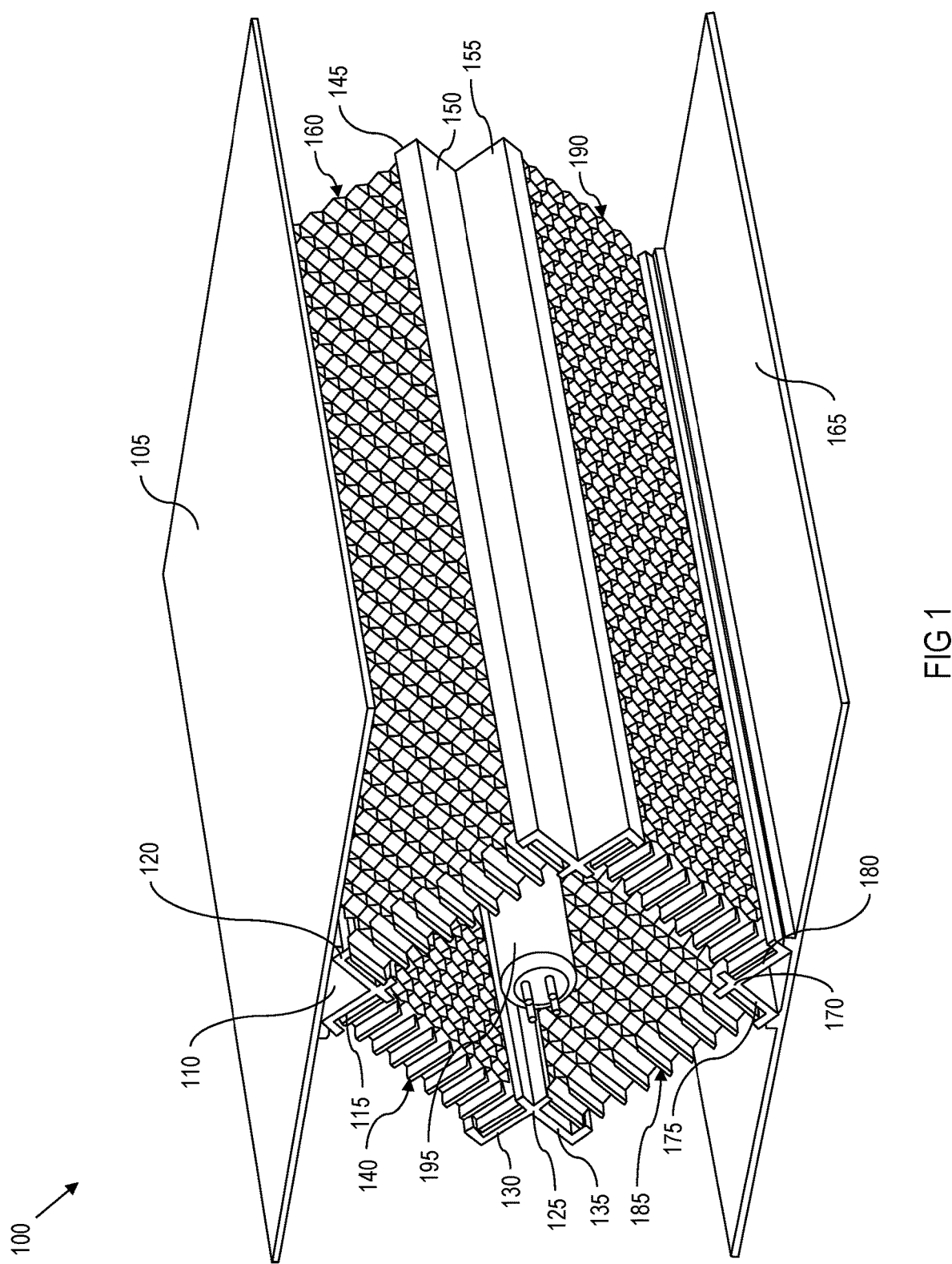
FIG. 1 is a diagram illustrating a photocatalytic system for reducing airborne contaminants.

Having provided a broad technical solution to a technical problem, reference is now made in detail to the description of the embodiments as illustrated in FIG. 1. While several embodiments are described in connection with these drawings, there is no intent to limit the disclosure to the embodiment or embodiments disclosed herein. On the contrary, the intent is to cover all alternatives, modifications, and equivalents.

Turning now to FIG. 1, described and taught is one embodiment of a photocatalytic system 100 for reducing airborne contaminants using an ultraviolet (UV) emitter 195. In the shown embodiment, the system 100 comprises a housing wall 105 (designated herein as a first housing wall 105 to distinguish this element from other housing walls (described below)). The first housing wall 105 is positioned non-perpendicular to a fluid flow path, meaning that the fluid does not flow in a path that is perpendicular to the first housing wall 105. The first housing wall 105 comprises a support 110 (for clarity, designated as a first support 110) that is mechanically coupled to the first housing wall 105.

The first support 110 comprises two (2) separate grooves 115, 120 (designated herein as first groove 115 and second groove 120). The first groove 115 is positioned at an angle (designated as first angle) on the first support 110. For the embodiment of FIG. 1, the first angle is approximately forty-five degrees (45°) from the first wall 105. The second groove 120 is positioned at a different angle (designated as second angle) on the first support 110. For the embodiment of FIG. 1, the second angle is 135°, thereby placing the first groove 115 at approximately right angles to the second groove 120.

The system 100 further comprises another support 125 (designated as a second support 125). Similar to the first support 110, the second support 125 also comprises two (2) separate grooves 130, 135 (designated herein as third groove 130 and fourth groove 135 to distinguish these from the first groove 115 and the second groove 120). For the embodiment of FIG. 1, the third groove 130 and the fourth groove 135 are placed at substantially right angles to each other. The third groove 130 substantially faces the first groove 115.

The system 100 of FIG. 1 further comprises a photocatalytic cell 140 (designated as a first photocatalytic cell 140 for clarity). The first photocatalytic cell 140 has two lateral edges, a front face, and a back face, a top edge, and a bottom edge. Preferably, the first photocatalytic cell 140 comprises a honeycomb matrix that allows the first photocatalytic cell 140 to be porous or permeable to flowing fluid (e.g., air flow). Each of the two (2) lateral edges (designated herein as a first edge and a second edge) are placed in the first groove 115 and the third groove 130, respectively. Because the first groove 115 holds the first edge of the first photocatalytic cell 140 and the third groove 130 (which faces the first groove 115) holds the second edge of the first photocatalytic cell 140, these two (2) grooves 115, 130, in combination, hold in place the first photocatalytic cell 140.

The system 100 further comprises another support 145 (designated as a third support 145 to distinguish this feature from the first support 110 and the second support 125). Similar to the first support 110 and the second support 125, the third support 145 also comprises two (2) separate grooves 150, 155 (for clarity, designated herein as fifth groove 150 and sixth groove 155). For the embodiment of FIG. 1, the fifth groove 150 and the sixth groove 155 are placed at substantially right angles to each other. The fifth groove 150 of the third support 145 substantially faces the second groove 120 of the first support 110.

The system 100 of FIG. 1 further comprises another photocatalytic cell 160 (designated as a second photocatalytic cell 160 to distinguish it from the first photocatalytic cell 140). Similar to the first photocatalytic cell 140, the second photocatalytic cell 160 has two lateral edges, a front face, and a back face, a top edge, and a bottom edge. Preferably, the second photocatalytic cell 160 comprises a honeycomb matrix that allows the second photocatalytic cell 160 to be porous or permeable to the air flow (or other flowing fluid). Each of the two (2) lateral edges (designated herein as a third edge and a fourth edge) are placed in the second groove 120 and the fifth groove 150, respectively. Because the second groove 120 holds the third edge of the second photocatalytic cell 160 and the fifth groove 150 (which faces the second groove 120) holds the fourth edge of the second photocatalytic cell 160, these two (2) grooves 120, 150, in combination, hold in place the second photocatalytic cell 160.

The system 100 of FIG. 1 further comprises another housing wall 165 (designated herein as second housing wall 165 to distinguish it from the first housing wall 105). The second housing wall 165 is positioned substantially parallel to the first housing wall 105 and, thus, is non-perpendicular to the direction of fluid flow. The second housing wall 165 comprises a support 170 (designated herein as a fourth support 170 to distinguish it from the other supports 110, 125, 145). The fourth support 170 is mechanically coupled to the second housing wall 165 and, also, has two (2) grooves 175, 180 (designated herein as a seventh groove 175 and an eighth groove 180). The seventh groove 175 is positioned at an angle (designated as seventh angle) to the second wall 165 (shown here as being approximately 45° to the second wall 165). The seventh groove 175 substantially faces the fourth groove 135 of the second support 125.

The eighth groove 180 is at a different angle (designated herein as eighth angle) to the second wall 165 (shown here as being approximately 135° to the second wall 165). For the system 100 of FIG. 1, the seventh groove 175 and the eighth groove 180 are shown to be at substantially a right angle to each other. The eighth groove 180 substantially facing the sixth groove 155 of the third support 145.

The system 100 of FIG. 1 comprises yet another photocatalytic cell 185 (designated as a third photocatalytic cell 185 to distinguish it from the first photocatalytic cell 140 and the second photocatalytic cell 160). Similar to the previously described photocatalytic cells 140, 160, the third photocatalytic cell 185 has two lateral edges, a front face, and a back face, a top edge, and a bottom edge. Preferably, the third photocatalytic cell 185 also comprises a honeycomb matrix that allows the third photocatalytic cell 185 to be porous or permeable to the air flow (or other flowing fluid). Each of the two (2) lateral edges (designated herein as a fifth edge and a sixth edge) are placed in the fourth groove 135 and the seventh groove 175, respectively. Because the fourth groove 135 holds the fifth edge of the third photocatalytic cell 185 and the seventh groove 175 (which faces the fourth groove 135) holds the sixth edge of the third photocatalytic cell 185, these two (2) grooves 135, 175, in combination, hold in place the third photocatalytic cell 185.

The system 100 of FIG. 1 comprises yet another photocatalytic cell 190 (designated as a fourth photocatalytic cell 190 to distinguish it from the previously described photocatalytic cells 140, 160, 185). Similar to the previously described photocatalytic cells 140, 160, 185, the fourth photocatalytic cell 190 has two lateral edges, a front face, and a back face, a top edge, and a bottom edge. Preferably, the fourth photocatalytic cell 190 also comprises a honeycomb matrix that allows the fourth photocatalytic cell 190 to be porous or permeable to the air flow (or other flowing fluid). Each of the two (2) lateral edges (designated herein as a seventh edge and an eighth edge) are placed in the sixth groove 155 and the eighth groove 180, respectively. Because the sixth groove 155 holds the seventh edge of the fourth photocatalytic cell 190 and the eighth groove 180 (which faces the sixth groove 155) holds the eighth edge of the fourth photocatalytic cell 190, these two (2) grooves 155, 180, in combination, hold in place the fourth photocatalytic cell 190.

The four photocatalytic cells 140, 160, 185, 190, in combination, form an enclosure for a UV emitter 195. For the embodiment of FIG. 1, two (2) photocatalytic cells (e.g., first photocatalytic cell 140 and third photocatalytic cell 185) are located in the fluid flow path before the UV emitter 195, while two (2) photocatalytic cells (e.g., second photocatalytic cell 160 and fourth photocatalytic cell 190) are located in the fluid flow path after the UV emitter 195.

Figure 2:
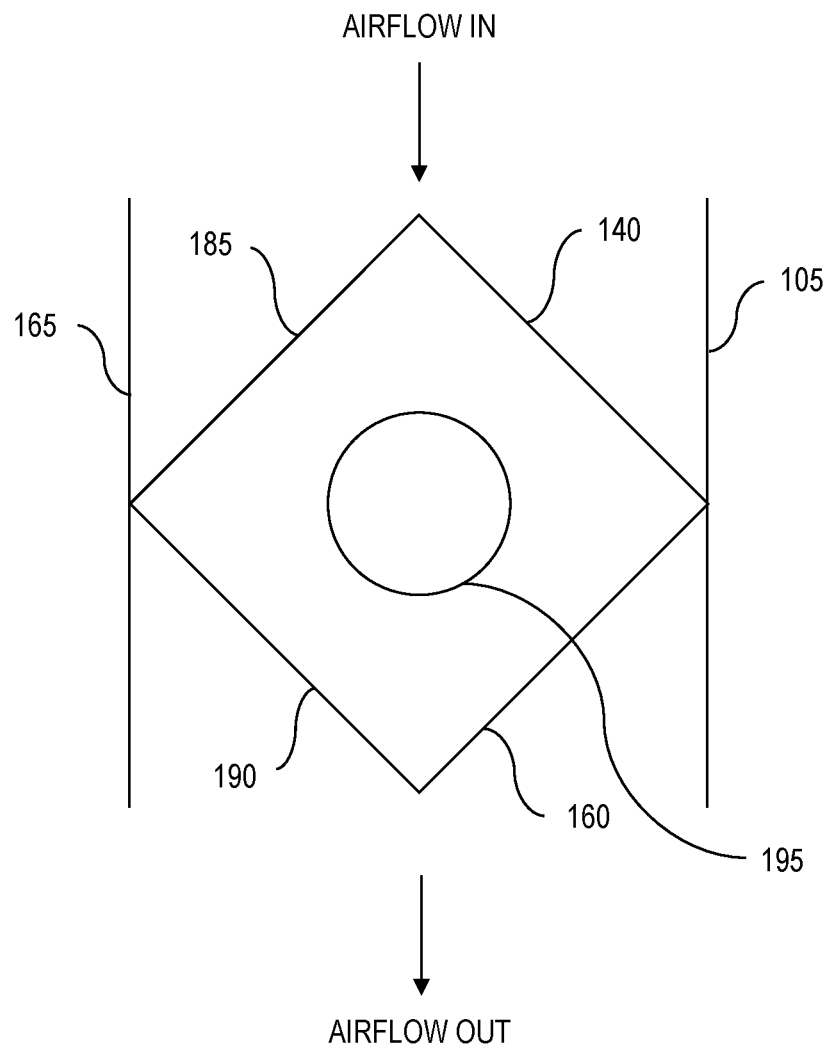
FIG. 2 is a diagram showing a cross-sectional view of the system of FIG. 1 with airflow through the system.

Thus, broadly described, the system 100 of FIG. 1 comprises four (4) photocatalytic cells (e.g., first photocatalytic cell 140, second photocatalytic cell 160, third photocatalytic cell 185, and fourth photocatalytic cell 190), which, in combination, substantially form porous walls of an enclosure for a UV emitter 195. For the embodiment of FIG. 1, each photocatalytic cell 140, 160, 185, 190 is positioned at an angle with reference to its adjacent photocatalytic cell 140, 160, 185, 190 in such a way that two (2) of the photocatalytic cells 140, 185 are located in the fluid flow path before the UV emitter 195, while two (2) remaining photocatalytic cells 160, 190 are located in the fluid flow path after the UV emitter 195. A cross-sectional view of the system, along with the direction of the fluid flow (labeled as airflow), is shown in FIG. 2.

In operation, by providing four (4) total photocatalytic cells 140, 160, 185, 190, the system 100 of FIG. 1 increases substantially the cells that produce ion clusters and, therefore, increases catalytic reactions that reduce airborne contaminants. Furthermore, providing the photocatalytic cells in a substantially angled configuration to each other permits relatively unimpeded airflow (or fluid flow) through the system 100.

Any process descriptions or blocks in flow charts should be understood as being performed out of order from that shown or discussed, including substantially concurrently or in reverse order, depending on the functionality involved, as would be understood by those reasonably skilled in the art of the present disclosure.

Although exemplary embodiments have been shown and described, it will be clear to those of ordinary skill in the art that a number of changes, modifications, or alterations to the disclosure as described may be made. All such changes, modifications, and alterations should therefore be seen as within the scope of the disclosure.

What is claimed is:

1. A photocatalytic system for reducing airborne contaminants using an ultraviolet (UV) emitter positioned in a fluid flow path, the system comprising:
    a first photocatalytic cell:
    a second photocatalytic cell positioned at a first angle to the first photocatalytic cell;
    a third photocatalytic cell positioned at a second angle to the first photocatalytic cell;
    a fourth photocatalytic cell positioned at a third angle to the second photocatalytic cell, the fourth photocatalytic cell further being positioned at a fourth angle to the third photocatalytic cell, a combination of the first photocatalytic cell, the second photocatalytic cell, the third photocatalytic cell, and the fourth photocatalytic cell forming porous walls of an enclosure for the UV emitter, the first photocatalytic cell and the second photocatalytic cell being located in the fluid flow path before the UV emitter, the third photocatalytic cell and the fourth photocatalytic cell being located in the fluid flow path after the UV emitter; and
    a first housing wall non-perpendicular to the fluid flow path, the first housing wall comprising:
        a first support mechanically coupled to the first housing wall, the first support comprising:
            a first groove positioned at a first non-perpendicular angle on the first support, the first groove for securing a first edge of the first photocatalytic cell; and
            a second groove positioned at a second non-perpendicular angle on the first support, the second non-perpendicular angle being different from the first non-perpendicular angle, the second groove for securing a first edge of the second photocatalytic cell.

2. The system of claim 1, wherein:
    the first angle is a right angle;
    the second angle is a right angle;
    the third angle is a right angle; and
    the fourth angle is a right angle.

3. The system of claim 1, wherein:
    the first photocatalytic cell comprises a honeycomb matrix;
    the second photocatalytic cell comprises a honeycomb matrix;
    the third photocatalytic cell comprises a honeycomb matrix; and
    the fourth photocatalytic cell comprises a honeycomb matrix.

4. The system of claim 1, further comprising:
    a second housing wall positioned parallel to the first housing wall, the second housing wall comprising:
        a second support mechanically coupled to the second housing wall, the second support comprising:
            a third groove positioned at a third non-perpendicular angle on the second support, the third groove for securing a first edge of the third photocatalytic cell; and
            a fourth groove positioned at a fourth non-perpendicular angle on the second support, the fourth non-perpendicular angle being different from the third non-perpendicular angle, the fourth groove for securing a first edge of the fourth photocatalytic cell.

5. The system of claim 4, further comprising:
    a third support comprising:
        a fifth groove facing the first groove, the fifth groove for securing a second edge of the first photocatalytic cell;
        a sixth groove facing the third groove, the sixth groove for securing a second edge of the third photocatalytic cell; and
    a fourth support comprising:
        a seventh groove facing the second groove, the seventh groove for securing a second edge of the second photocatalytic cell; and
        an eighth groove positioned facing the fourth groove, the eighth groove for securing a second edge of the fourth photocatalytic cell.

6. A photocatalytic system for reducing airborne contaminants using an ultraviolet (UV) emitter, the system comprising:
    a first housing wall non-perpendicular to a fluid flow path, the first housing wall comprising:
        a first support mechanically coupled to the first housing wall, the first support comprising:
            a first groove positioned at a first angle on the first support;
            a second groove positioned at a second angle on the first support, the second angle being different from the first angle;
        a second support comprising:
            a third groove facing the first groove, the third groove being positioned at a third angle on the second support;
            a fourth groove positioned at a fourth angle on the second support;
    a first photocatalytic cell comprising:
        a first edge positioned in the first groove; and
        a second edge positioned in the third groove;
    a third support comprising:
        a fifth groove facing the second groove, the fifth groove being positioned at a fifth angle on the third support;
        a sixth groove positioned at a sixth angle on the third support;
    a second photocatalytic cell comprising:
        a third edge positioned in the second groove; and
        a fourth edge positioned in the fifth groove;
    a second housing wall positioned parallel to the first housing wall, the second housing wall comprising:
        a fourth support mechanically coupled to the second housing wall, the fourth support comprising:
            a seventh groove facing the fourth groove, the seventh groove being positioned at a seventh angle on the fourth support; and
            an eighth groove facing the sixth groove, the eighth groove being positioned at an eighth angle on the fourth support, the eighth angle being different from the seventh angle;

a third photocatalytic cell comprising:
  a fifth edge positioned in the fourth groove; and
  a sixth edge positioned in the seventh groove; and
a fourth photocatalytic cell that, in combination with the first photocatalytic cell, the second photocatalytic cell, and the third photocatalytic cell, forms an enclosure for the UV emitter, the fourth photocatalytic cell comprising:
  a seventh edge positioned in the sixth groove; and
  an eighth edge positioned in the eighth groove.

7. The system of claim 6, wherein:
the first photocatalytic cell comprises a first honeycomb matrix;
the second photocatalytic cell comprises a second honeycomb matrix;
the third photocatalytic cell comprises a third honeycomb matrix; and
the fourth photocatalytic cell comprises a fourth honeycomb matrix.

8. The system of claim 6, wherein:
the first angle is at a right angle to the second angle;
the third angle is at a right angle to the fourth angle;
the fifth angle is at a right angle to the sixth angle; and
the seventh angle is at a right angle to the eighth angle.

* * * * *